United States Patent [19]

Inagaki et al.

[11] Patent Number: 4,845,298

[45] Date of Patent: Jul. 4, 1989

[54] PROCESS FOR PREPARATION OF UNSATURATED LONG-CHAIN ALIPHATIC SECONDARY AMINE

[75] Inventors: Takeo Inagaki, Chiba; Akira Fukasawa, Yachiyo; Hiroshi Yamagishi, Tokyo, all of Japan

[73] Assignee: Lion Akzo Company Limited, Tokyo, Japan

[21] Appl. No.: 7,219

[22] Filed: Jan. 27, 1987

[30] Foreign Application Priority Data

Jan. 27, 1986 [JP] Japan .................. 61-15255

[51] Int. Cl.$^4$ ............................. C07C 85/12
[52] U.S. Cl. ................................... 564/490
[58] Field of Search ............... 564/490; 260/409

[56] References Cited

U.S. PATENT DOCUMENTS

| | | | |
|---|---|---|---|
| 2,355,356 | 8/1944 | Young | 564/490 |
| 2,784,232 | 3/1957 | Terry et al. | 564/490 |
| 2,811,556 | 10/1957 | Shapiro | 564/490 |
| 4,161,483 | 7/1979 | Cahen | 260/409 |
| 4,229,361 | 10/1980 | Cahen | 260/409 |
| 4,683,088 | 7/1987 | Oudejans et al. | 564/490 |

FOREIGN PATENT DOCUMENTS

| | | |
|---|---|---|
| 1135291 | 4/1957 | France . |
| 55-9018 | 1/1980 | Japan . |
| 759291 | 10/1956 | United Kingdom . |
| 773432 | 4/1957 | United Kingdom . |
| 1475689 | 6/1977 | United Kingdom . |
| 2025408 | 7/1978 | United Kingdom . |

OTHER PUBLICATIONS

Comptes Rendus, vol. 224, 1947, pp. 478-479.

Primary Examiner—Glennon H. Hollrah
Assistant Examiner—A. A. Owens
Attorney, Agent, or Firm—Armstrong, Nikaido, Marmelstein, Kubovcik & Murray

[57] ABSTRACT

A process for selectively preparing an unsaturated long-chain aliphatic secondary amine at a high yield comprising reducing an unsaturated aliphatic nitrile having 8 to 22 carbon atoms or a nitrile mixture containing said nitrile with hydrogen in the presence of a Ni hydrogenation catalyst and a carboxylic acid amide at a reaction temperature of 160° C. to 200° C.

5 Claims, No Drawings

PROCESS FOR PREPARATION OF UNSATURATED LONG-CHAIN ALIPHATIC SECONDARY AMINE

BACKGROUND OF THE INVENTION

1. Field of the Invention

The present invention relates to an improved process for the preparation of unsaturated long-chain aliphatic secondary amines by reducing unsaturated long-chain aliphatic nitriles with hydrogen.

2. Description of the Related Art

Amines having long-chain alkyl groups are generally prepared by reducing long-chain aliphatic nitriles, derived from natural fats and oils, with hydrogen. When long-chain aliphatic nitriles are reduced with hydrogen, a mixture of primary, secondary, and tertiary amines are obtained. Among these amines, unsaturated long-chain aliphatic secondary amines are advantageous in that the quaternary ammonium salts thereof can provide softness and antistaticity to various fabrics and hair, and in addition, can be used as a softener for providing excellent water absorbability and handling ease to the treated fabrics. Therefore, a process for selectively preparing secondary amines at a high yield is desired.

Known processes for the preparation of unsaturated long-chain aliphatic secondary amines are the reduction of unsaturated long-chain aliphatic nitriles with hydrogen using a Cu-Cr catalyst (BP 773,432) or an Ni hydrogenation catalyst (USP 2,355,356, USP 2,784,232, BP 759,291, Japan Kokai 55-9018). The former process has a disadvantage in that a longer reaction time is necessary because of the low activity of the Cu-Cr catalyst, and the latter process gives only a poor selectivity of unsaturated long-chain aliphatic secondary amines because most of the unsaturated bonds in aliphatic chains are hydrogenated while the nitrile radicals are converted to amino radicals.

SUMMARY OF THE INVENTION

Accordingly, the objects of the present invention are to eliminate the above-mentioned disadvantages of the prior art and to provide a process for preparing an unsaturated long-chain aliphatic secondary amine at a good selectivity and at a high yield from an unsaturated long-chain aliphatic nitrile or a nitrile mixture containing said nitrile.

Other objects and advantages of the present invention will be apparent from the following description.

In accordance with the present invention, there is provided a process for preparing an unsaturated long-chain aliphatic secondary amine comprising reducing an unsaturated aliphatic nitrile having 8 to 22 carbon atoms or a nitrile mixture containing said nitrile with hydrogen in the presence of Ni hydrogenation catalysts and an carboxylic acid amides at a reaction temperature of 160° C. to 200° C.

DESCRIPTION OF THE PREFERRED EMBODIMENTS

It is generally known in the reaction to convert unsaturated long-chain aliphatic nitriles to secondary amines in the presence of Ni hydrogenation catalysts that, when the reduction of nitrile radicals to amino radicals is accelerated, it is hard to obtain unsaturated long-chain aliphatic secondary amines in high selectivity because the hydrogenation of unsaturated bonds in aliphatic chains is also accelerated, and conversely, under the conditions needed to suppress the hydrogenation of unsaturated bonds in aliphatic chains, it is difficult to obtain unsaturated long-chain aliphatic secondary amines in high yield, since the speed of the amination reaction is reduced.

As mentioned above, in the process provided by the present invention, the reduction of unsaturated long-chain aliphatic nitriles with hydrogen using Ni hydrogenation catalysts is carried out at 160°–200° C. in the presence of carboxylic acid amides. Under these conditions, the hydrogenation of unsaturated bonds in aliphatic chains is suppressed but the conversion of nitrile radicals to amino radicals is promoted, and consequently, unsaturated long-chain aliphatic secondary amines can be obtained at a good selectivity and a high yield.

The unsaturated long-chain aliphatic nitriles used as a starting material in the present invention are unsaturated long-chain aliphatic or fatty nitriles having 8 to 22 carbon atoms or mixtures of nitriles containing said nitriles, e.g., nitriles prepared from oleic acid, linoleic acid, linolenic acid, erucic acid, tallow fatty acid, soya fatty acid, palm oil fatty acid, tall oil fatty acid, and rape fatty acid.

The catalysts usable in the present invention are nickel hydrogenation catalysts, especially those supported on a carrier such as kieselguhr, alumina, silica-alumina and so on. The preferable amount of the catalyst added is 0.1 to 0.5 parts by weight based on 100 parts by weight of the starting nitrile.

The carboxylic acid amides usable in the process of the present invention are saturated or unsaturated aliphatic carboxylic acid amides having 1 to 22 carbon atoms or aromatic carboxylic acid amides having 7 to 22 carbon atoms. These carboxylic acid amides can be used alone or as a mixture of two or more. The saturated or unsaturated carboxylic acid amides used in the present invention can be, for example, acetamide, propionamide, butyramide, 2-ethylhexylamide, lauramide, stearamide, oleamide, erucamide, coco fatty acid amide, tallow fatty acid amide, or cyclohexane carboxylic acid amide.

The aromatic carboxylic acid amides used can be, for example, benzamide, phenylacetamide, phenylpropionamide, cinnamic acid amide, 4-methyl benzamide, or benzanilide.

The preferable amount of the carboxylic acid amide added is 0.03% to 3% by mole, based on the mole amount of the nitrile. When the aliphatic carboxylic acid amide is used, preferably the amount of addition is 0.3 to 3% by mole, and when an aromatic carboxylic acid amide is used, preferably the amount of addition is 0.03 to 1% by mole. When the amount of the carboxylic acid amide added is less than the preferable amount, the hydrogenation of the unsaturated bonds in the aliphatic chains tends not to be sufficiently suppressed, and on the other hand, when the amount of the carboxylic acid amide added is more than the preferable amount, the yield of the desired secondary amines tends to be lowered in accordance with the decrease in the rate of reduction of the nitrile radical.

In the practice of the present invention, it is essential to maintain the reaction temperature within a limited range of between 160° C. and 200° C. to obtain a high yield of secondary amines having a large content of unsaturated bonds in aliphatic chains. When the reaction temperature exceeds 200° C., the unsaturated bonds in aliphatic chains are hydrogenated faster, and consequently, the obtained secondary amines contain less unsaturated bonds in their aliphatic chains. When reaction temperature is lower than 160° C., the yield of secondary amines decreases in accordance with the reduced rate of conversion of the nitrile radicals to amino radicals.

The hydrogen pressure in the process of the present invention is not specifically limited as long as it is equal to or higher than atmospheric pressure, but from the economical point of view, the hydrogen pressure is preferably less than 10 kg/cm2G.

The process of the present invention is carried out by agitating a mixture of the above-mentioned nitrile, catalyst, and carboxylic acid amide charged into a reactor at a temperature of 160°–200° C. while allowing hydrogen to flow through the mixture.

The process of the present invention can provide a mixture of amines having unsaturated long-chain aliphatic secondary amines as the main component. This mixture comprises 70%, preferably 75%, or more of unsaturated bonds in aliphatic chains in the nitriles of the starting material, and a selectivity to secondary amine and a conversion of nitriles to amines are 80%, preferably 85% or more, and 97% or more, respectively.

EXAMPLES

The present invention will now be further illustrated by, but is by no means limited to, the following Examples.

EXAMPLE 1

Into a 1 liter autoclave were charged 500 g of oleonitrile, 1 g of Ni-kieselguhr catalyst, and 1.2 g of acetamide (1.07% by mole based on the mole amount of nitrile). Hydrogen was passed through the mixture while stirring. The hydrogen pressure was maintained at 3 kg/cm 2G, and the contents of the autoclave were heated. The temperature was raised to 180° C., and the flow of hydrogen was continued through the mixture while stirring at 180° C. for 2 hrs; the hydrogen pressure was maintained at 3 kg/cm2G.

After the reaction, the mixture was cooled to 100° C. and the catalyst removed by filtration. The amine mixture thus obtained contained 5.2% of primary amine, 89.1% of secondary amine and 5.1% of tertiary amine. The iodine value of this amine mixture is 86.6% of Theoretical Iodine Value (iodine value of amine mixture when nitriles of starting material are converted to secondary amines at a 100% selectivity and 100% yield, and in addition, all of the unsaturated bonds in fatty chains remain after the reaction. This also applies to the following Examples and Comparative Examples). The results are thus obtained are shown in Table 1.

EXAMPLES 2–6 and COMPARATIVE Example 1

The reactions were carried out in the manner described in Example 1 except that the kind and the amount of the carboxylic acid amides added was changed.

The results are shown in Table 1.

TABLE 1

| Example No. or Comparative Example No. | | Example | | | | | | Com. Ex. |
|---|---|---|---|---|---|---|---|---|
| | | 1 | 2 | 3 | 4 | 5 | 6 | 1 |
| Carboxylic acid amide | Kind | acetamide | lauramide | oleamide | benzamide | 4-methyl benzamide | benzanilide | none |
| | Amount (g) of addition | 1.2 | 5 | 5 | 1 | 1 | 1.5 | |
| | mole %/nitrile | (1.07) | (1.32) | (0.94) | (0.43) | (0.39) | (0.40) | |
| Composition of amine mixture | Prim. Am. (%) | 5.2 | 5.0 | 6.1 | 5.1 | 5.4 | 5.8 | 5.2 |
| | Sec. Am. (%) | 89.1 | 88.0 | 88.1 | 87.5 | 87.2 | 87.8 | 89.1 |
| | tert. Am. (%) | 5.1 | 5.3 | 4.8 | 5.4 | 5.6 | 5.8 | 4.9 |
| $\frac{\text{IV of product}}{\text{Theoretical IV}} \times 100$ (%) | | 86.6 | 81.2 | 80.7 | 94.3 | 91.2 | 92.7 | 69.1 |

EXAMPLES 7–8 AND COMPARATIVE EXAMPLES 2–3

Into a 1 liter autoclave were charged 500 g of oleonitrile, 1 g of Ni-kieselguhr catalyst, and 1 g of benzamide (0.43% by mole based on the mole amount of the nitrile). The reactions were carried out in a manner as described in Example 1 except that the reaction temperature was changed to each of those shown in Table 2. After the reaction, the amine mixture was obtained by removing the catalyst in the manner described in Example 1.

The results are shown in Table 2.

TABLE 2

| Example No. or Comparative Example No. | | Example | | Com. Ex. | |
|---|---|---|---|---|---|
| | | 7 | 8 | 2 | 3 |
| Reac. Temp. (°C.) | | 190 | 170 | 210 | 150 |
| Composition of amine mixture | Prim. Am. (%) | 4.6 | 6.6 | 3.7 | 9.4 |
| | Sec. Am. (%) | 89.2 | 86.1 | 91.2 | 81.4 |
| | Tert. Am. (%) | 4.7 | 5.3 | 4.4 | 5.2 |
| $\frac{\text{IV of product}}{\text{Theoretical IV}} \times 100$ (%) | | 87.4 | 96.1 | 71.6 | 97.6 |

EXAMPLE 9

Into a 1 liter autoclave were charged 500 g of tallow nitrile (IV = 50.9), 1 g of Ni-kieselguhr catalyst, and 0.5 g of benzamide (0.22% by mole based on the mole amount of the nitrile). The reaction was carried out and the catalyst removed in the manner described in Example 1. The amine mixture thus obtained contained 4.7% of primary amines, 86.4% of secondary amines, and 8.2% of tertiary amines. The iodine value of this amine mixture is 87.0% of Theoretical Iodine Value.

EXAMPLE 10

Into a 1 liter autoclave were charged 500 g of soya nitrile (IV = 112.7), 1 g of Ni-kieselguhr, and 1.5 g of acetamide (1.32% by mole based on the mole amount of nitrile). The reaction was carried out and the catalyst removed in the manner described in Example 1. The amine mixture thus obtained contained 5.4% of primary amines, 89.2% of secondary amines and 4.8% of tertiary amines. The iodine value of this amine mixture is 83.9% of Theoretical Iodine Value.

EXAMPLES 11-14

The reactions were carried out in the manner described in Example 1 except that the amount of acetamide added was changed to each of those shown in Table 3.

The results are shown in Table 3.

TABLE 3

| Example No. | | Example | | | |
|---|---|---|---|---|---|
| | | 11 | 12 | 13 | 14 |
| Amount of acetamide | g | 3 | 0.5 | 4.5 | 0.2 |
| | (mole %/ nitrile) | (2.67) | (0.45) | (4.01) | (0.18) |
| Composition of amine mixture | Prim. Am. (%) | 5.5 | 5.9 | 3.7 | 5.3 |
| | Sec. Am. (%) | 86.2 | 89.1 | 83.4 | 89.4 |
| | Tert. Am. (%) | 5.8 | 4.5 | 2.6 | 4.9 |
| $\frac{\text{IV of product}}{\text{Theoretical IV}} \times 100\ (\%)$ | | 89.2 | 78.2 | 92.4 | 72.1 |

EXAMPLES 15-18

The reactions were carried out in the manner described in Example 4 except that the amount of benzamide added was changed to each of those shown in Table 4.

The results are shown in Table 4.

TABLE 4

| Example No. | | Example | | | |
|---|---|---|---|---|---|
| | | 15 | 16 | 17 | 18 |
| Amount of acetamide | g | 2 | 0.1 | 3 | 0.05 |
| | (mole %/ nitrile) | (0.87) | (0.043) | (1.30) | (0.022) |
| Composition of amine mixture | Prim. Am. (%) | 5.4 | 5.6 | 5.3 | 5.8 |
| | Sec. Am. (%) | 86.3 | 88.9 | 82.0 | 89.2 |
| | Tert. Am. (%) | 5.8 | 4.3 | 6.7 | 4.2 |
| $\frac{\text{IV of product}}{\text{Theoretical IV}} \times 100\ (\%)$ | | 96.7 | 76.0 | 98.2 | 71.4 |

We claim:

1. A process for preparing an unsaturated long-chain aliphatic secondary amine which comprises selectively reducing the nitrile group in an unsaturaed aliphatic nitrile having 8 to 22 carbon atoms or a nitrile mixture containing said nitrile with hydrogen in the presence of a Ni hydrogenation catalyst and a carboxylic acid amide at a reaction temperature of 160° C. to 200° C.

2. A process as claimed in claim 1, wherein said carboxylic acid amide is an aliphatic carboxylic acid amide.

3. A process as claimed in claim 2, wherein the amount of said aliphatic carboxylic acid amide added is 0.3% to 3% by mole based on the mole amount of the unsaturated aliphatic nitriles having 8 to 22 carbon atoms.

4. A process as claimed in claim 1, wherein said carboxylic acid amide is an aromatic carboxylic acid amide.

5. A process as claimed in claim 4, wherein the amount of said aromatic carboxylic acid amide added is 0.03% to 1% by mole based on the mole amount of the unsaturated aliphatic nitriles having 8 to 22 carbon atoms.

* * * * *